(12) United States Patent
Lashgari et al.

(10) Patent No.: US 10,925,508 B2
(45) Date of Patent: Feb. 23, 2021

(54) ATRIAL FLUTTER DETECTION UTILIZING NONLINEAR DIMENSION REDUCTION

(71) Applicant: PACESETTER, INC., Sylmar, CA (US)

(72) Inventors: Elnaz Lashgari, Anaheim Hills, CA (US); Stuart Rosenberg, Woodbury, MN (US); Fujian Qu, San Jose, CA (US)

(73) Assignee: PACESETTER, INC., Sylmar, CA (US)

( * ) Notice: Subject to any disclaimer, the term of this patent is extended or adjusted under 35 U.S.C. 154(b) by 66 days.

(21) Appl. No.: 16/194,123

(22) Filed: Nov. 16, 2018

(65) Prior Publication Data
US 2020/0155023 A1 May 21, 2020

(51) Int. Cl.
| | | |
|---|---|---|
| *A61B 5/04* | (2006.01) | |
| *A61B 5/046* | (2006.01) | |
| *A61N 1/362* | (2006.01) | |
| *A61N 1/37* | (2006.01) | |
| *A61B 5/0464* | (2006.01) | |
| *A61B 5/0468* | (2006.01) | |
| *A61B 5/0456* | (2006.01) | |
| *A61B 5/0472* | (2006.01) | |

(Continued)

(52) U.S. Cl.
CPC .......... *A61B 5/046* (2013.01); *A61B 5/04012* (2013.01); *A61B 5/0464* (2013.01); *A61B 5/0468* (2013.01); *A61N 1/3624* (2013.01); *A61N 1/3702* (2013.01); *A61B 5/0456* (2013.01); *A61B 5/0472* (2013.01); *A61B 5/686* (2013.01); *A61B 5/7264* (2013.01); *A61B 5/7282* (2013.01); *A61N 1/3956* (2013.01)

(58) Field of Classification Search
CPC ... A61B 5/046; A61B 5/04012; A61B 5/0464; A61B 5/0468; A61B 5/0456; A61B 5/0472; A61B 5/7282; A61B 5/686; A61B 5/7264; A61N 1/3624; A61N 1/3702; A61N 1/3956
See application file for complete search history.

(56) References Cited

U.S. PATENT DOCUMENTS

2013/0096394 A1\* 4/2013 Gupta .................. A61B 5/4848
600/301

OTHER PUBLICATIONS

Roweis et al. "Nonlinear Dimensionality Reduction by Locally Linear Embedding" Science vol. 290; Dec. 2000 (4 pages).
(Continued)

*Primary Examiner* — Rex R Holmes
(74) *Attorney, Agent, or Firm* — The Small Patent Law Group LLC; Dean D. Small

(57) ABSTRACT

A computer implemented method and system for declaring arrhythmias in cardiac activity are provided. The method and system are under control of one or more processors that are configured with specific executable instructions. The method and system obtain far field cardiac activity (CA) signals for a series of beats and builds an N-dimensional data set from data values for features of interest from the CA signals. The method and system utilize a manifold structure to map the N-dimensional data set, through nonlinear dimensional reduction, onto an M-dimensional data set and declares an atrial fibrillation (AFL) episode based on a relation between the M-dimensional data set and one or more AFL classification criteria.

20 Claims, 8 Drawing Sheets

(51) Int. Cl.
*A61N 1/39* (2006.01)
*A61B 5/00* (2006.01)

(56) References Cited

OTHER PUBLICATIONS

Cayton "Algorithms for Manifold Learning" Jun. 2005 (17 pages).
Saul et al. "Think Globally, Fit Locally: Unsupervised Learning of Low Dimensional Manifolds" Journal of Machine Learning Research vol. 4; 2003 (37 pages).

* cited by examiner

| A-V Conduction Pattern | Flutter Cycle Length (ms) | Ventricular Rate (bpm) |
|---|---|---|
| 2:1 | 210 | 142 |
| 2:1 | 200 | 150 |
| 2:1 | 190 | 158 |
| 3:1 | 210 | 95 |
| 3:1 | 200 | 100 |
| 3:1 | 190 | 105 |
| 4:1 | 210 | 71 |
| 4:1 | 200 | 75 |
| 4:1 | 190 | 79 |

Figure 5B

ATRIAL FLUTTER DETECTION UTILIZING NONLINEAR DIMENSION REDUCTION

FIELD OF THE INVENTION

Embodiments herein relate generally to detection and discrimination of atrial flutter waves in cardiac activity signals utilizing a nonlinear dimension reduction.

BACKGROUND OF THE INVENTION

Atrial Flutter (AFL) refers to a set of arrhythmias that originate in reentrant circuits inside the atria. The rate of AFL is usually from 240 to 340 per minute, with 300 per minute commonly observed. An electro-cardiogram (ECG) presentation of atrial flutter appears as a series of saw tooth or picket fence flutter waves that may exhibit different ratios between atrial and ventricular events, such as 2:1, 3:1, and higher. AFL may commonly occur in patients at risk for atrial arrhythmias as well as patients treated with pulmonary vein isolation ablation procedures to treat atrial fibrillation (AF).

Today, commercially released implantable cardiac monitors (ICMs) and implantable medical devices (IMDs) utilize AF detection algorithms that detect atrial fibrillation. However, conventional AF detection algorithms are not well suited to accurately detect AFL and discriminate it from AF. In part, conventional AF detection algorithms experience difficulty in detecting AFL because AFL events have a large variation in morphology and have a small amplitude relative to R-waves and T-waves.

Also, conventional AF detection algorithms experience difficulty in detecting AFL because ventricular rates associated with AFL may be lower than rates that are programmed for a tachycardia threshold. When an AFL episode occurs with a ventricular rate that is lower than programmed tachycardia threshold, the AFL events are never logged for clinicians to review. Further, conventional AF detection algorithms detect arrhythmias based on variability in the R-wave to R-wave (R-R) interval (RRI) over a series of cardiac beats. Even when an AFL episode exhibits a high ventricular rate, the patient experiences an R-R interval that is often sufficiently regular that the AF detection algorithm does not declare as an AF detection.

If AFL episodes could be recognized, the arrhythmia can be effectively treated by identification of the flutter circuit and ablating across the reentrant path.

An opportunity remains to develop AFL detection algorithms for use by implantable devices.

SUMMARY

In accordance with embodiments herein, a computer implemented method for declaring arrhythmias in cardiac activity is provided. The method is under control of one or more processors that are configured with specific executable instructions. The method obtains far field cardiac activity (CA) signals for a series of beats and builds an N-dimensional data set from data values for features of interest from the CA signals. The method utilizes a manifold structure to map the N-dimensional data set, through nonlinear dimensional reduction, onto an M-dimensional data set and declares an atrial fibrillation (AFL) episode based on a relation between the M-dimensional data set and one or more AFL classification criteria.

Optionally, the manifold structure may utilize locally linear embedding to provide the nonlinear dimensional reduction to form the M-dimensional data set. Optionally, N may be greater than or equal to 100 dimensions, and M may be less than or equal to 10 dimensions. The method may divide the CA signals into RR interval (RRI) segments that may be normalized to a select cycle length having a common number of non-prioritized sample positions during each of the RRI segments. The building operation may comprise populating dimensions of the N-dimensional data set with CA data values for the non-prioritized sample positions from the RRI segments. The dimensions of the N-dimensional data set may correspond to the non-prioritized sample positions along the select cycle length.

Optionally, the method may automatically calculate the manifold structure utilizing a non-linear dimensionality reduction technique that may automatically determine an underlying structure of data points within the N-dimensional data set. The method may program the manifold structure into firmware of an implantable device to configure the implantable device to utilize the manifold structure in real time in connection with declaring AFL episodes. The method may analyze the N-dimensional data set, at a local external or remote server, to automatically calculate the manifold structure based on locally linear embedding to provide the nonlinear dimensional reduction.

Optionally, the method may determine whether a select number of RRI segments from the CA signals fall within a predetermined common ventricular rate range. The predetermined common ventricular rate range may correspond to an integer conduction multiple of a predetermined AFL rate, and based on the determining, may declare a candidate AFL episode to be analyzed through the building, utilizing and declaring operations. The declaring the candidate AFL episode may further comprise applying clustering criteria to the RRI segments of the CA signals that fall within the predetermined common ventricular rate range. The clustering criteria may correspond to a predetermined number of RRI segments that may fall within a predetermined cluster range of one another.

In accordance with embodiments herein, a system for declaring arrhythmias in cardiac activity is provided. The system comprises memory to store specific executable instructions. One or more processors are configured to execute the specific executable instructions for obtaining far field cardiac activity (CA) signals for a series of beats and building an N-dimensional data set from data values for features of interest from the CA signals. The system utilizes a manifold structure to map the N-dimensional data set, through nonlinear dimensional reduction, onto an M-dimensional data set and declares an atrial fibrillation (AFL) episode based on a relation between the M-dimensional data set and one or more AFL classification criteria.

Optionally, the manifold structure may utilize locally linear embedding to provide the nonlinear dimensional reduction to form the M-dimensional data set. Optionally, N may be greater than or equal to 100 dimensions, and M may be less than or equal to 10 dimensions. The one or more processors may be further configured to divide the CA signals into RR interval (RRI) segments that may be normalized to a select cycle length having a common number or non-prioritized sample positions during each of the RRI segments, and may populate dimensions of the N-dimensional data set with CA data values for the non-prioritized sample positions from the RRI segments.

Optionally, the one or more processors may be further configured to automatically calculate the manifold structure utilize a non-linear dimensionality reduction technique that automatically determines an underlying structure of data points within the N-dimensional data set. The system may comprise an implantable device that may house the memory and the one or more processors. The memory may be configured to store the manifold structure. The one or more processors may be configured to utilize the manifold structure in real time in connection with declaring AFL episodes.

Optionally, the system may comprise an external device or server that may house the one or more processors that may be further configured to analyze the N-dimensional data set to automatically calculate the manifold structure based on locally linear embedding to provide the nonlinear dimensional reduction. The one or more processors may be further configured to determine whether a select number of RR interval (RRI) segments from the CA signals fall within a predetermined common ventricular rate range. The predetermined common ventricular rate range may correspond to an integer conduction multiple of a predetermined AFL rate, and based on the determining, may declare a candidate AFL episode to be analyzed through the building, utilizing and declaring operations. An implantable medical device may house the one or more processors and memory. The one or more processors and memory may be housed within at least one of an external device or a server.

BRIEF DESCRIPTION OF THE DRAWINGS

FIG. 5B illustrates a table of example ventricular rate ranges that may be utilized in accordance with embodiments herein.

DETAILED DESCRIPTION

Figure 1:
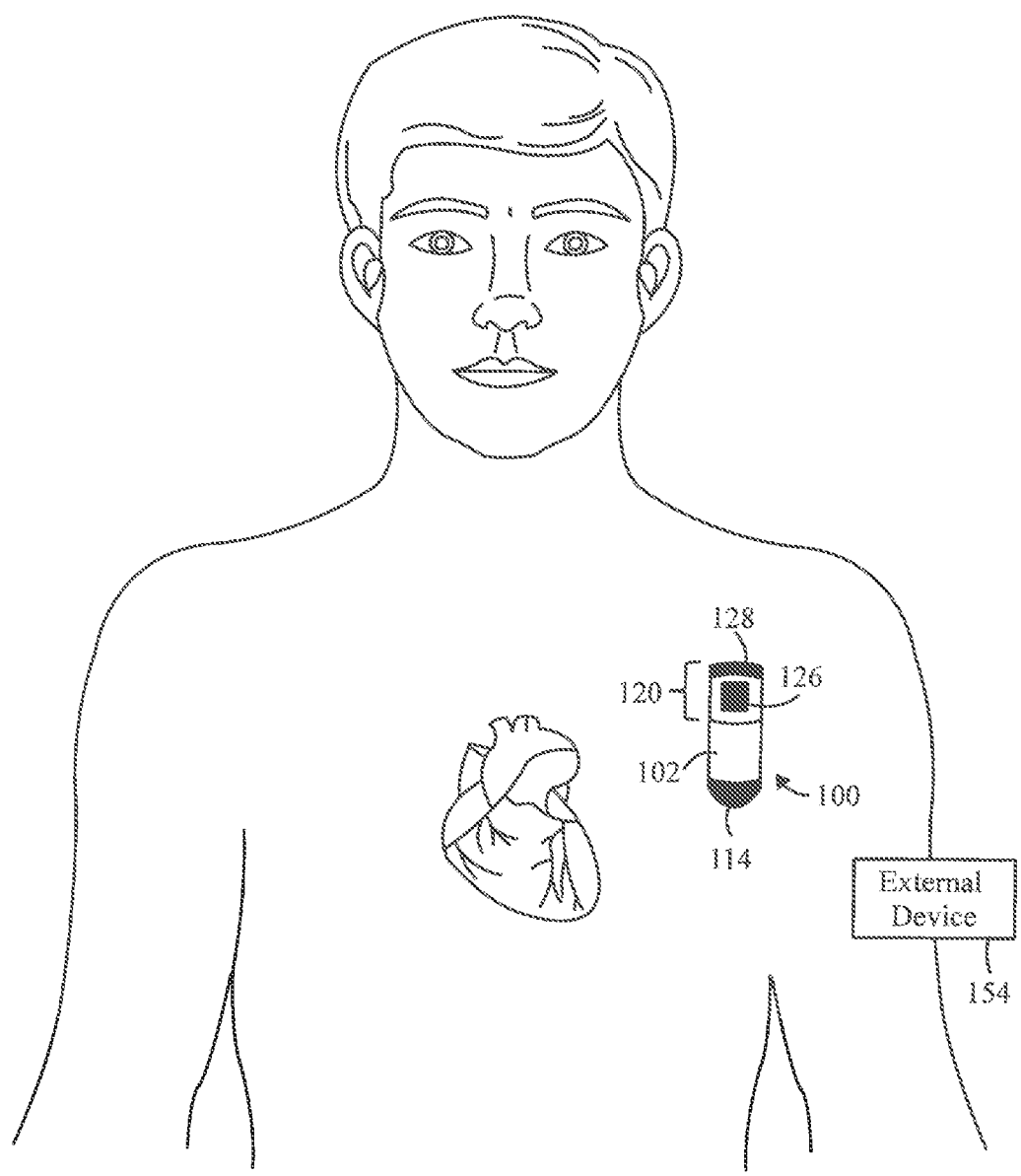
FIG. 1 illustrates an ICM intended for subcutaneous implantation at a site near the heart in accordance with embodiments herein.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The terms "cardiac activity data set" and "CA data set" (collectively "CA data set") are used interchangeably to refer to a data set that includes measured CA signals for a series of cardiac events in combination with device documented markers.

The term "marker" refers to data and/or information identified from CA signals that may be presented as graphical and/or numeric indicia indicative of one or more features within the CA signals and/or indicative of one or more episodes exhibited by the cardiac events. Markers may be superimposed upon CA signals or presented proximate to, and temporally aligned with, CA signals. Non-limiting examples of markers may include R-wave markers, noise markers, activity markers, interval markers, refractory markers, P-wave markers, T-wave markers, PVC markers, sinus rhythm markers, AF markers and other arrhythmia markers. As a further nonlimiting example, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor during the CA signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

The term "device documented marker" refers to markers that are declared by an implantable cardiac monitor and/or implantable medical device. Any or all of the foregoing examples of markers represent device document markers. Markers may be declared based on numerous criteria, such as signal processing, feature detection and AF detection software and hardware within and/or operating on the implantable cardiac monitor and/or implantable medical device.

The terms "beat" and "cardiac event" are used interchangeably and refer to both normal or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, a un-healthy or abnormal functioning of the heart.

The term "real-time" refers to a time frame contemporaneous with occurrence of a normal or abnormal episode. For example, a real-time process or operation would occur during or immediately after (e.g., within minutes or seconds after) a cardiac event, a series of cardiac events, an arrhythmia episode, and the like.

The term "obtain", as used in connection with data, signals, information and the like, includes at least one of i) accessing memory of an IMD, ICM, external device or remote server where the data, signals, information, etc. are stored, ii) receiving the data, signals, information, etc. over a wireless communications link between the ICM or IMD and a local external device, and/or iii) receiving the data, signals, information, etc. at a remote server over a network connection. An obtaining operation, when from the perspective of an ICM or IMD, may include sensing new signals in real time, and/or accessing memory to read stored data, signals, information, etc. from memory within the ICM or IMD. The obtaining operation, when from the perspective of a local external device, includes receiving the data, signals, information, etc. at a transceiver of the local external device where the data, signals, information, etc. are transmitted from an ICM and/or a remote server. The obtaining operation may be from the perspective of a remote server, such as when receiving the data, signals, information, etc. at a network interface from a local external device and/or directly from an ICM. The remote server may also obtain the data, signals, information, etc. from local memory and/or from other memory, such as within a cloud storage environment and/or from the memory of a workstation or clinician external programmer.

FIG. 1 illustrates an ICM 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and if an arrhythmia is detected, automatically records the CA signals in memory for subsequent transmission to an external device. The CA signal processing and AF detection is provided for, at least in part, by algorithms embodied in or implemented by the microprocessor. The ICM 100 includes one or more processors and memory that stores program instructions directing the processors to implement AF detection utilizing an on-board R-R interval irregularity (ORI) process that analyzes cardiac activity signals collected over one or more sensing channels.

Figure 2:
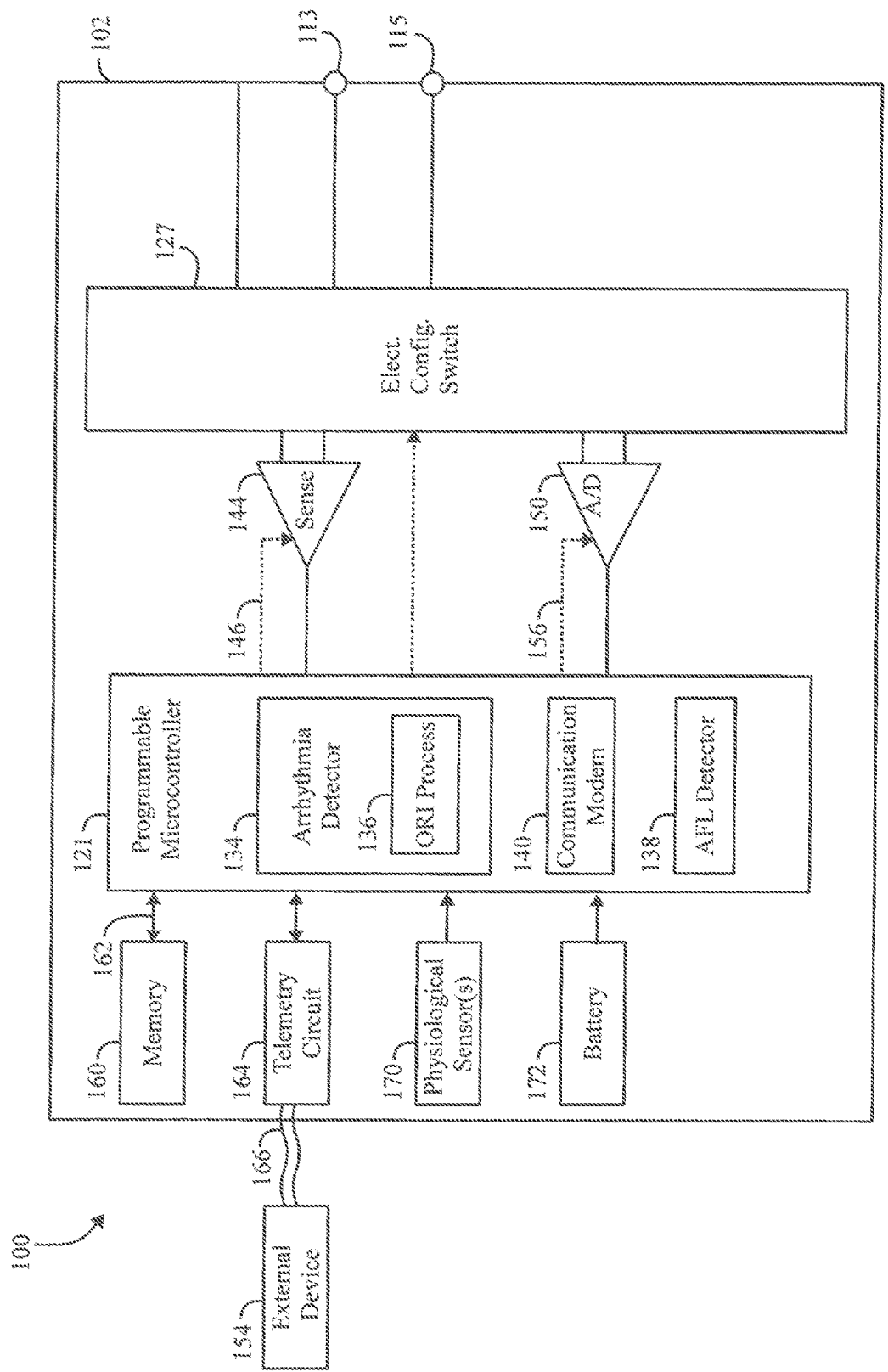
FIG. 2 shows a block diagram of the ICM formed in accordance with embodiments herein.

FIG. 2 shows a block diagram of the ICM 100 formed in accordance with embodiments herein. The ICM 100 may be implemented to monitor ventricular activity alone, or both ventricular and atrial activity through sensing circuit. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126.

Microcontroller 121 includes an arrhythmia detector 134 that is configured to analyze cardiac activity signals to identify potential AF episodes as well as other arrhythmias (e.g., Tachcardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies. The arrhythmia detector 134 of the microcontroller 121 includes an on-board R-R interval irregularity (ORI) process 136 that detects AF episodes using R-R interval irregularities. The ORI process 136 may be implemented as firmware, software and/or circuits. The ORI process 136 uses a hidden Markov Chains and Euclidian distance calculations of similarity to assess the transitionary behavior of one R-wave (RR) interval to another and compare the patient's RR interval transitions to the known RR interval transitions during AF and non-AF episodes obtained from the same patient and/or many patients.

The microcontroller 121 also includes an AFL detector 138 that is configured to implement the operations described herein. Among other things, the AFL detector 138 is configured for obtaining far field cardiac activity (CA) signals for a series of beats. The AFL detector 138 is configured to build an N-dimensional data set from data values for features of interest from the CA signals. The AFL detector 138 is configured to utilize a manifold structure to map the N-dimensional data set, through nonlinear dimensional reduction, onto an M-dimensional data set; and declare an AFL episode based on a relation between the M-dimensional data set and one or more AFL classification criteria. The manifold structure utilizes locally linear embedding to provide the nonlinear dimensional reduction to form the M-dimensional data set. For example, N is greater than or equal to 100 dimensions, and wherein M is less than or equal to 10 dimensions. The AFL detector 138 may be further configured to divide the CA signals into RR interval segments that are normalized to a select cycle length having a common number of sample positions, and to populate dimensions of the N-dimensional data set with CA data values for the sample positions from the CA signals. The AFL detector 138 may be further configured to automatically calculate the manifold structure utilize a non-linear dimensionality reduction technique that automatically determines an underlying structure/rhythm of the data points within the N-dimensional data set. Optionally, the memory may be configured to store the manifold structure in firmware, and the AFL detector 138 configured to utilize the manifold structure in real time in connection with declaring AFL episodes. The AFL detector 138 may be further configured to analyze the N-dimensional data set to automatically calculate the manifold structure based on locally linear embedding to provide the nonlinear dimensional reduction. The AFL detector 138 may be configured to determine whether a select number of RR intervals from the CA signals fall within a predetermined common ventricular rate range, wherein the predetermined common ventricular rate range corresponds to an integer conduction multiple of a predetermined AFL rate. Based on the determination, the AFL detector 138 may declare a candidate AFL episode to be analyzed through the building, utilizing and declaring operations.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuit 144 selectively coupled to one or more electrodes that perform sensing operations, through the switch 127 to detect cardiac activity data indicative of cardiac activity. The sensing circuit 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuit 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the A/D data acquisition system 150) in the memory 160 when a potential AF episode is detected. The sensing circuit 144 receives a control signal 146 from the microcontroller 121 for purposes of controlling the gain, threshold, polarization charge removal circuitry (not shown), and the timing of any blocking circuitry (not shown) coupled to the inputs of the sensing circuit.

Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the CA signals from the A/D data acquisition system 150 directly coupled to the electrodes.

The ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential AF episodes. The ACS adjustment and ORI process 136 may be applied to signals from the sensing circuit 144 and/or the DAS 150.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See for example, U.S. Pat. No. 7,294,108, Cardiac event micro-recorder and method for implanting same, which is hereby incorporated by reference.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, bradycardia rate, tachycardia rate, tachycardia cycle count). The amount of CA data storage may vary based upon the size of the memory 160.

The ICM 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 3A:
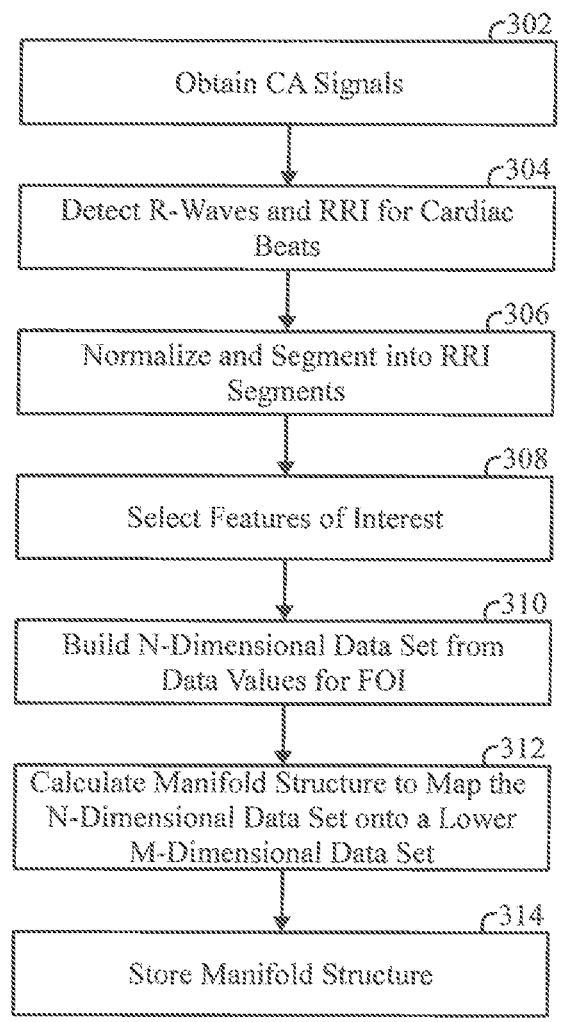
FIG. 3A illustrates a process for building a model to analyze CA signals to detect atrial flutter episodes in accordance with embodiments herein.

FIG. 3A illustrates a process for building a model to analyze CA signals to declare AFL episodes in accordance with embodiments herein. The operations of FIG. 3A may be implemented, in whole or in part by one or more processors of an ICM, IMD, local external device, remote server, and/or a combination thereof.

At 302, one or more processors of the system obtain reference cardiac activity (CA) signals, or a reference CA data set that includes CA signals, recorded in connection with a series of cardiac events/beats. The reference CA signals include CA signals for reference cardiac beats known to include atrial fibrillation and for reference cardiac beats known to be normal and not include atrial fibrillation. For example, one or more 30 second EGM strips may be utilized as a reference data set where the EGM strip has CA signals that are known to include atrial fibrillation. As a further example, different one or more 30 second EGM strips may be utilized as a reference data set where the EGM strip has CA signals that are known to be under normal rhythm. Additionally or alternatively, reference CA data sets may be recorded for a variety of patients, recorded by a variety of device types, device placements, device orientations and the like.

Additionally or alternatively, the obtaining operation at 302 may represent a collection of new CA signals/data set that may be triggered based on the analysis for "candidate AFL episodes" as described herein.

The CA data includes device documented rhythmic markers (e.g., R-wave markers) that identify the cardiac beats sensed by the device within the series of cardiac events. For example, the device documented markers may be declared and designated by the ICM utilizing an ORI process to analyze the CA signals. ECG and/or EGM signals may be collected by a subcutaneous ICM that does not include a transvenous lead or otherwise experiences difficulty in sensing P-waves and/or R-waves. The cardiac activity data may have been previously acquired and stored in memory of an implantable or external monitoring device, implantable or external therapy delivery device, programmer, workstation, healthcare network or other system. When the cardiac activity data has been previously acquired, the obtaining operation at 302 represents accessing and reading the previously stored cardiac activity data.

The operations of FIG. 3A may be staged to be performed upon the CA signals at various times. The CA signals may be read out of the ICM to a local portable external device and transmitted to a remote server, medical network, physician computer and the like, which implements all or a portion of the operations described in connection with FIG. 3A remote from the patient. Additionally or alternatively, the CA signals may be read from the ICM by a programmer device, such as during a patient visit to a physician, where the programmer device implements all or a portion of the operations described in connection with FIG. 3A during or after a patient-doctor visit.

The CA signals are for one or more series of cardiac events spanning over various periods of time. As one example, multiple segments or sets of the cardiac activity data may be collected, where each segment/set is for an interval that is 30 seconds to 5 minutes in length. Optionally, the segments may include one or more ICM declared AFL episodes. As another example, each of the segments or sets of the cardiac activity data may be collected for an interval that begins 10-60 seconds before an episode of interest (e.g., an AF episode) and that ends 10-60 seconds after the episode of interest. The CA signals may include one or multiple AFL episodes. The CA data sets obtained at 302 may include one or more detected AFL episodes and/or one or more cardiac beats confirmed to be normal with no AFL episodes. The CA data set obtained at 302 may correspond to one continuous series of cardiac events (e.g., 1 continuous series for 30 seconds to 5 minutes) and/or separate sets of cardiac events (5, 10 or more separate series, each for 30 seconds to 5 minutes of cardiac events).

Collection and analysis of CA signals by the ICM may be initiated automatically when the ICM detects an AFL episode of interest. Additionally or alternatively, the ICM may collect and analyze CA signals in response to a user-initiated instruction or clinician. For example, a user or clinician may utilize a smart phone, programmer or other portable device to establish a communications session with the ICM and instruct the ICM to begin to collect and analyze cardiac signals, such as when the patient is experiencing discomfort, feeling faint, a rapid heart rate, during a clinic visit, etc.

At 304, the one or more processors analyze the CA signals to detect R-waves therein and to calculate RR intervals between successive cardiac beats. At 306, the one or more processors divide the RR intervals (RRIs) into RRI segments. Each RRI segment substantially corresponds to one cardiac cycle. At 306, the one or more processors also apply a normalization function to the RRI segments to normalize a number of samples in each of the cardiac cycles. The normalization function may normalize a length of each of the RRI segments (corresponding to cardiac cycles) to have a select (e.g., standard) cycle length having a common number of sample positions, where the number of sample positions corresponds to a "longest" cardiac cycle (e.g., the cardiac cycle having a greatest number of sample positions relative to other cardiac cycles in the series of cardiac beats). The normalization may be implemented in various manners. Shorter RRI segments may be "stretched" by the processors by adding synthetic data values and sample positions between actual data sample positions, where the synthetic data values and sample positions are calculated by interpolation, averaging and the like. Optionally, the lengths of the RRI segments may be normalized to a predetermined (e.g., an average) cycle length. RRI segments that are shorter than the average cycle length are "stretched" by adding synthetic data samples. RRI segments that are longer than the average cycle length are "shrunk" by merging 2 or more actual data samples to form a smaller set of 1 or more synthetic data samples.

Each of the normalized RRI segments is utilized as a separate individual data point in the subsequent operations of FIG. 3A. As described herein, the normalized RRI segments are used as individual input points into a high dimensional space.

At 308, the one or more processors select a collection of features of interest from the normalized RR segments from the CA signals to be extracted. The features of interest are non-prioritized and are independent of physiological characteristics (e.g., not R-waves, P-waves, T-waves). By way of example, the features of interest may correspond to non-prioritized sample positions along the standard cycle length (e.g., along the normalized RRI segments). The sample positions are "non-prioritized" as the sample positions are distributed evenly (or unevenly) along the standard cycle length with regard for the position of the R-wave or other physiologic characteristics. The sample positions are independent of specific physiologic characteristics of the cardiac cycle, such as independent of the R-wave, P-wave, T-wave, etc. For example, an individual normalized RRI segment may include 100, 1000, or more sample positions, each of which has a corresponding CA data value (e.g., a voltage level in millivolts). As a further example, when each normalized RRI segment is divided into 1000 equally spaced sample positions (having corresponding CA data values), the collection would similarly include 1000 independent features of interest (FOI).

Figure 3B:
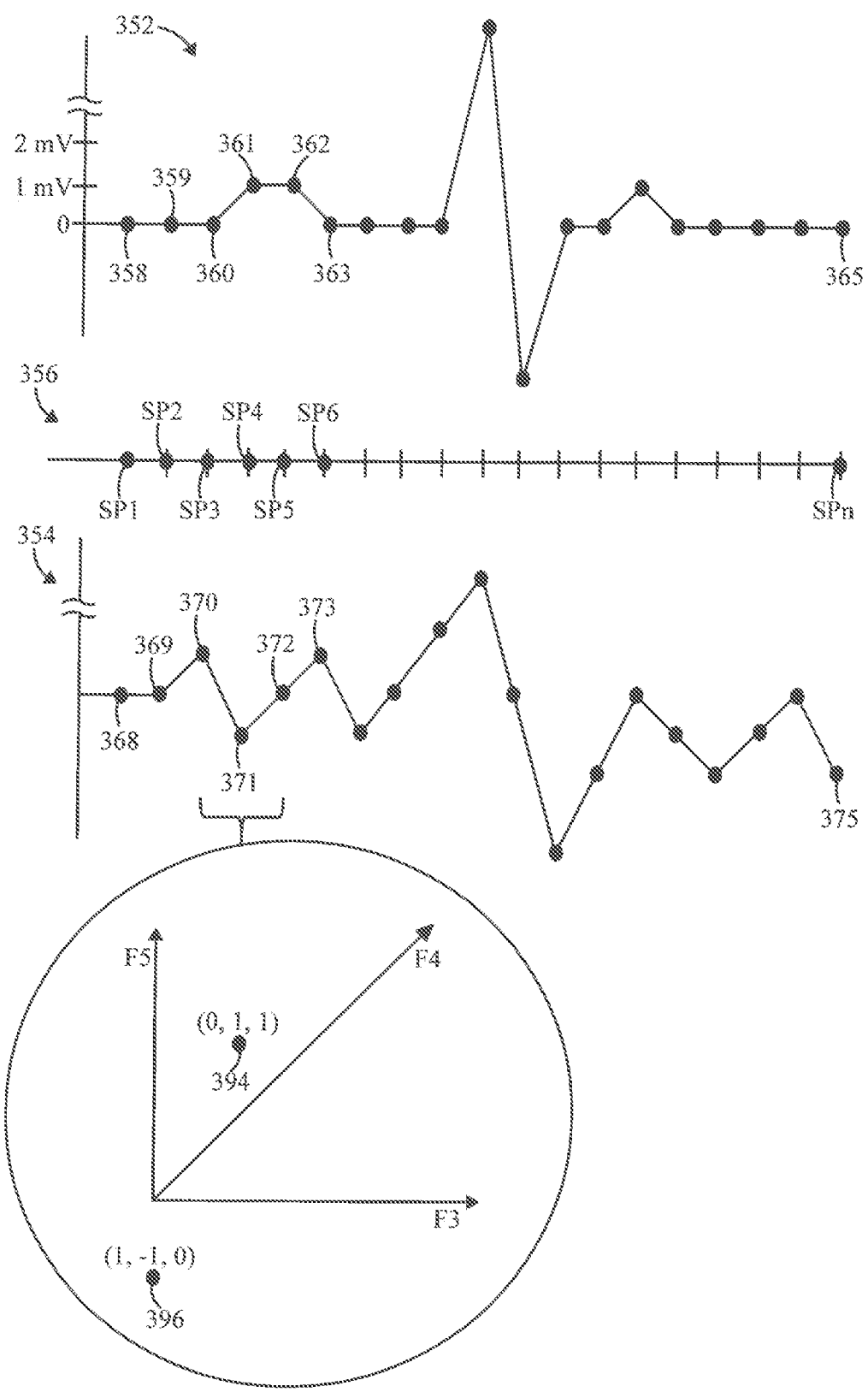
FIG. 3B illustrates an example collection of features of interest utilized in accordance with an embodiment herein.

FIG. 3B illustrates an example collection of features of interest utilized in accordance with an embodiment herein. FIG. 3B illustrates CA signals for first and second beats 352, 354 associated with first and second cardiac cycles. The horizontal axis corresponds to time (e.g., milliseconds), while the vertical axis corresponds to voltage (e.g., millivolts). It is recognized that the time and voltage levels shown in FIG. 3B are not to scale, but instead R-waves are generally much larger than P-waves, T-waves and AFL waves. The CA signals for the first and second beats 352, 354 have been normalized and segmented into RRI segments having a standard cycle length 356. Optionally, the RRI segments may also be normalized in amplitude. The first beat 352 exhibits very little flutter and instead includes a morphology similar to a normal cardiac cycle having a distinct P-wave, R-wave and T-wave. The second beat 354 exhibits atrial flutter in combination with at least a distinguishable R-wave. The processors select, as features of interest, sample positions SP1-SPn that are evenly distributed at an even regular interval over the standard cycle length 356, where dots represent CA data values 358-365 and 368-375 along the CA signals for the first and second beats 352, 354. While only first and second beats 352, 354 are illustrated, it is recognized that a large number of beats are collected over several seconds or several minutes to be analyzed in accordance with FIG. 3A. Also, it is recognized that an actual implementation would utilize a much larger number of sample positions than illustrated.

With respect to the selection at 308, the sample position SP1 corresponds to a first feature (e.g., feature F1) that has CA data values 358, 368 in the first and second beats 352, 354, respectively. Similarly, the second sample position SP2 correspond to a second feature (e.g., feature F2) that has CA data values 359, 369 in the beats 352, 354, while the third sample position SP3 correspond to a third feature (e.g., feature F3) that has CA data values 360, 370 in the beats 352, 354, and so forth for all of the sample positions up to the last sample position SPn and last feature Fn. For example, when the standardized cycle length is normalized into 1000 evenly spaced sample positions, similarly the operation at 308 would select 1000 FOI. Optionally, the processors may chose fewer than all of the sample positions along the standard cycle length. Additionally or alternatively, the processors may select one or more FOI other than sample positions. For example, the processors may include RRI, R-wave peaks, T-wave peaks, P-wave peaks, etc., as physiologic related FOI in addition to or in place of one or more of the non-physiologic related FOI (e.g., sample positions).

At 310, the one or more processors extract the CA data values at the select sample positions for the CA signals for a desired number of beats. The processors build an N-dimensional data set from the extracted CA data values. Individual dimensions of the N-dimensional data set correspond to an associated sample position along the standard cycle length. The CA data values 358-365 and 368-375 are utilized to build an N-dimensional data set, such as a data set having dimensions F1-Fn.

Returning to the example of FIG. 3B, a simplified portion of an N-dimensional data set is illustrated as a three dimensional data set. In the example of FIG. 3B, the three dimensions correspond to features F3-F5 which also correspond to sample points SP3-SP5. The CA data values 360-362, 370-372 for sample points SP3-SP5 are extracted and used to populate two data points within the 3D data set. Data point 394 corresponds to the first beat 352 and is loaded at coordinate/location (0,1,1) into the 3D data set based on the CA data values 360-362 which equal 0, 1 mV, 1 mV. Data point 396 corresponds to the second beat 354 and is loaded at coordinate/location (1. −1,0) into the 3D data set based on the CA data values 370-372 which equal 1 mV, −1 mV, 0. The example of FIG. 3B is expanded for multiple beats and for N-dimensions (e.g., n-sample positions, n-features).

In the foregoing manner, each feature represents a dimension in a high dimensional space, where each RRI segment is treated as a point in the high dimensional space. Cardiac activity signals may exhibit a large range of variation due, in part, to selection of different patients within a group of patients, different RRI segments for cardiac activity from a single patient, and different sampling pulses in a single patient. When the CA signals exhibit large variation, the CA signals similarly exhibit a large range in features. Even though a large feature range can exist, embodiments herein avoid extracting only features that are considered "important" in order to reduce the high dimensionality of the features that are to be analyzed. Instead, embodiments herein select a subset of the available features for extraction without regard for the physical interpretation of the features. Embodiments herein do not prioritize the features when selecting the subset of features. In contrast, methods such as principal component analysis, allow explicit identification of which features within the CA signals are considered most important.

At 312, the one or more processors analyze the N-dimensional data set and automatically calculate/discover a manifold structure that can be embedded onto the N-dimensional data set to map the N-dimensional data set onto a lower dimension M-dimensional data set having dimensions associated with intrinsic features that are indicative of AFL. For example, the M-dimensional data set may have 10 or fewer dimensions, and as a further example five dimensions.

The processors automatically calculate/discover the model/manifold structure utilize a non-linear dimensionality reduction technique that automatically determines an underlying structure/rhythm of the data points within the N-dimension data set. The processors calculate/discover the manifold utilizing locally linear embedding (LLE) for nearest neighbors for nonlinear dimensionality reduction. The nearest neighbors correspond to a predetermined number of neighbors surrounding each data point. By way of example, the processors may calculate the manifold utilizing the LLE techniques described in the article by Roweis and Saul, titled "Nonlinear Dimensionality Reduction by Locally Linear Embedding", published in Science, Vol. 290, Dec. 22, 2000, the complete subject matter of which is incorporated herein by reference in its entirety. In accordance with embodiments, the underlying manifold is calculated utilizing nonlinear dimensionality reduction of LLE, which differs from linear dimensionality reductions techniques of principal component analysis (PCA) and multidimensional scaling (MDS). Linear dimensionality reductions techniques of PCA and MDS create linear embeddings of manifolds onto a data set which maps faraway data points onto nearby points in a plane, which creates distortions in both the local and global geometry. The nonlinear embedding of LLE is capable of generating highly nonlinear embeddings and at least one main optimization involves a sparse eigenvalue problem that scales well to large high dimensional data sets.

Additionally or alternatively, the processors may calculate the manifold utilizing the techniques described in 1) an article by Saul and Roweis, titled "Think Globally, Fit Locally: Unsupervised Learning of Low Dimensional Manifolds", published in the Journal of Machine Learning Research 4 (2003), pages 119-155, and/or 2) an article by L. Cayton, titled "Algorithms for manifold learning" (2005), published in Technical Report CS 2008-0923, University of California, San Diego, the complete subject matter of which are incorporated herein by reference in their entireties.

In accordance with at least some embodiments, when reference CA signals are utilized that have known cardiac patterns (e.g., exhibit AFL or do not exhibit AFL), the processors are able to automatically build a manifold having a high degree of accuracy in reducing the N-dimensional data space to a lower dimension M-dimensional data space where the dimensions of the M-dimensional data space corresponds to features that strongly correlate to a presence or absence of AFL. The manifold is configured to afford dimensional reduction to obtain a more compact representation of the original data set (the data values at the N sample positions for all of the cardiac cycles in the CA signals). Nonlimiting examples of the dimensions/features that define the M-dimensional data space include a number of T-waves exhibited in each RRI segment, the RR interval duration, a number of changes in the direction of the CA signal, a relation between an amount of energy within the QRS complex and an amount of energy within the CA signal outside the QRS complex for a corresponding beat, a number of local peaks within the CA signal for an individual beat that have similar energy, peaks and/or frequency, and the like.

Figure 3C:
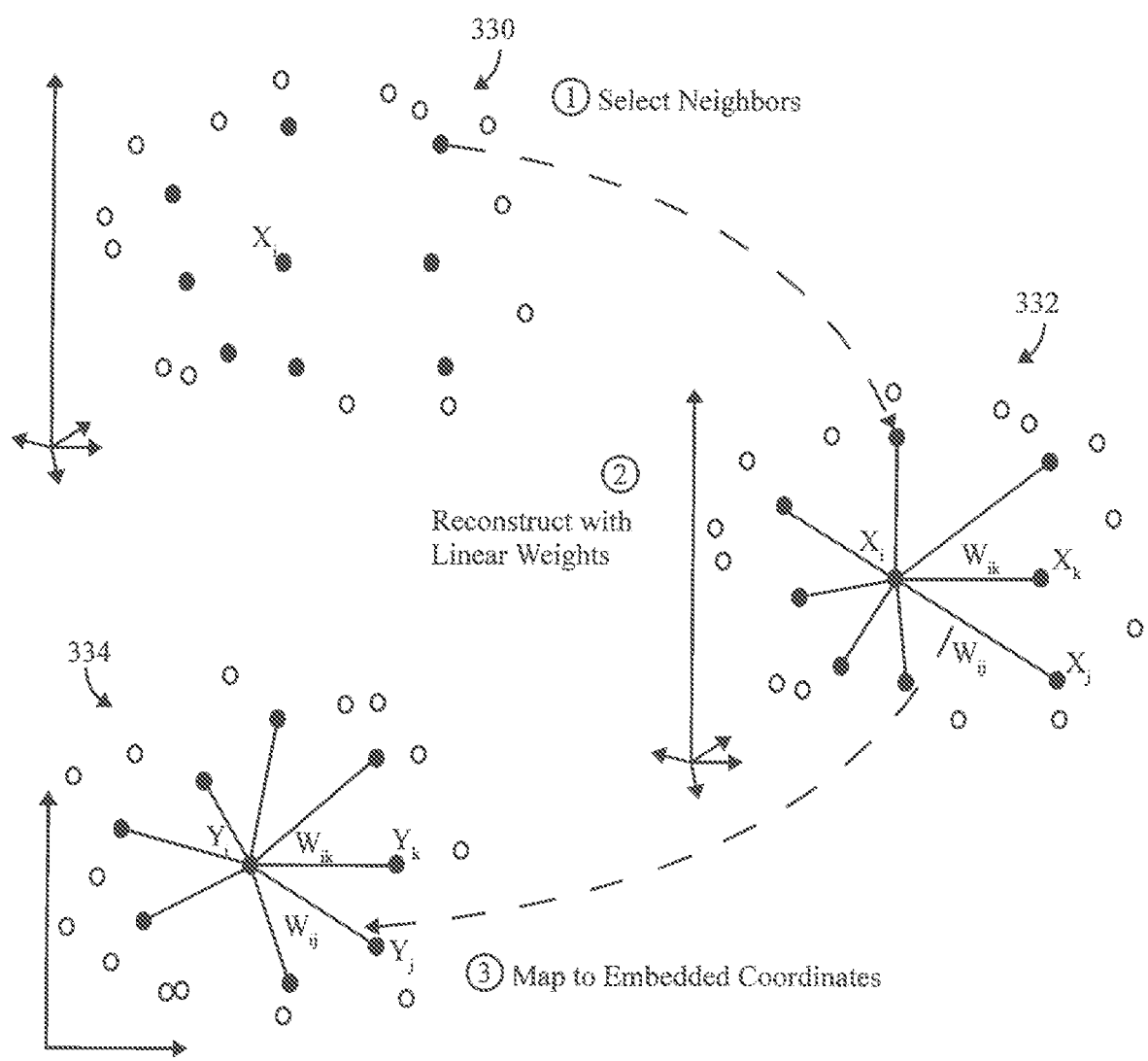
FIG. 3C illustrates a graphical representation of a manner in which a manifold may be automatically learned/discovered in connection with a linearly local collection of samples in accordance with embodiments herein.

FIG. 3C illustrates a graphical representation of a manner in which a manifold may be automatically learned/discovered in connection with a linearly local collection of samples. At 330, the processors individually analyze each data point within the high dimension, N-dimensional data space, and compute neighbors for each of the corresponding data points. For example, the processors identify a predetermined number of K nearest neighbors per data point as measured by Euclidean distance. In general, the LLE process attempts to compute a low dimensional embedding of a manifold with the property that nearby points in the high dimensional space remain nearby and similarly are co-located with respect to one another in the low dimensional space. The embedding seeks to preserve the local configurations of the predetermined number of nearest neighbors. The LLE process operates independent of and entirely without recourse to measures of distance or relation between faraway data points. At 330, the processors select a group of neighbors that lie on or closely to a locally linear patch of the manifold, where the curvature and sampling density are such that each data point has a number of neighbors that define an approximately linear patch on the manifold with respect to at least one dimension in the N-dimensional data space. The processors characterize a local geometry in the predetermined neighborhood of each data point by linear coefficients that reconstruct the data point from the neighbors of the data point.

At 332, the processors then calculate reconstruction errors that are measured by a cost function which adds up the squared distances between all of the data points and their reconstructions according to the following equation (1): $E(W)=\Sigma_i |X_i - \Sigma_j W_{ij} X_j|^2$, where $X_i$ represents an input data point, $X_j$ represents a $j^{th}$ nearest neighbor and $\Sigma_j W_{ij} X_j$ represents a locally linear reconstruction, with the reconstruction weights constrained to satisfy $\Sigma_j W_{ij}=1$. The processors compute weights that best reconstruct each data point from the neighbors of the corresponding data point, where the weights seek to minimize a cost associated with a constrained linear fit.

At 334, the processors map each high N-dimensional input data point $X_i$ to a low M-dimensional output data point $Y_i$ representing global internal coordinates on the manifold. The processors perform the foregoing mapping by choosing the M-dimensional coordinates of each output data point $Y_i$ to minimize an embedding cost function, such as according to the following equation (2): $\phi(Y)=\Sigma_i |Y_i - \Sigma_j W_{ij} Y_j|^2$, where $Y_i$ represents an output data point, and $Y_j$ represents a $j^{th}$ nearest neighbor and $\Sigma_j W_{ij} Y_j$ represents a locally linear reconstruction. At 334, the processors compute eigenvectors that are reconstructed by the weights in connection with minimizing a quadratic form of the equation to utilizing a select number of the eigenvectors. The operation for calculating the manifold structure enables the processors to achieve an accurate recognition by constructing a weighted graph for each data point and a set of edges connecting neighboring points and then embedding the manifold in the lower M-dimensional space.

By way of example, the cost function in equation 2 may be rewritten in a quadratic form: $\phi(Y)=\Sigma_{ij} M_{ij} (Y_i * Y_j)$, involving inner products of the outputs $Y_j$, where S represents a cost matrix. The processors find one or more of the top n+1 eigenvectors of the cost matrix, S. The top eigenvectors correspond to the largest eigenvalues. The top eigenvectors define embedding coordinates found by the LLE.

At 314, the one or more processors store the manifold structure for use in connection with analyzing subsequent CA signals. In accordance with the operations of FIG. 3A, once the manifold structure is discovered through a manifold learning process based on one or more reference data set, the manifold may be stored/programmed into various types of implantable devices, local external devices and/or remote servers. For example, the manifold structure may be stored in memory of an implantable device and configure the implantable device to utilize the manifold structure in real time in connection with declaring AFL episodes.

In accordance with the operations of FIG. 3A, embodiments herein allow the feature selection operation to be tuned/adjusted to identify AFL, such as by utilizing select training data sets of AFL cardiac rhythms and non-AFL rhythms. By way of example, the feature selection operation may be tuned/adjusted by changing the normalization scale, changing the number of sample positions utilized, and the like. As a further example, sample positions may be distributed closer to one another in regions preceding and following the R-wave, while sample positions aligned with the QRS complex may be distributed further from one another. Optionally, no sample positions may be utilized during the QRS complex of the RRI segments, such that the N-dimensions are defined by sample positions in a region of a cardiac cycle preceding the QRS complex and following the QRS complex. Additionally or alternatively, the N-dimensional data set may be populated by information other than amplitudes of CA data values. For example, a slope/derivative of the CA signal at each sample position may be determined and utilized to populate the N-dimensional data set.

Once a model has been generated that includes a select number of intrinsic features of interest, the model may be programmed into memory in an implantable device (ICM or IMD). The model may then be utilized to detect atrial flutter in real time contemporaneous with sensing of new cardiac activity. Additionally or alternatively, the operations for learning and adapting the model may be implemented at a remote server. For example, a remote server may analyze prerecorded data sets, such as in connection with fine-tuning atrial flutter detection models for certain subclasses of patients. The adapted model may be implemented in a cloud environment, whereby a remote server pushes the model back to an implantable device, such as through a local external device. The remote server provides instructions to direct the implantable device to update the implantable device firmware to add or adapt a model.

Figure 4:
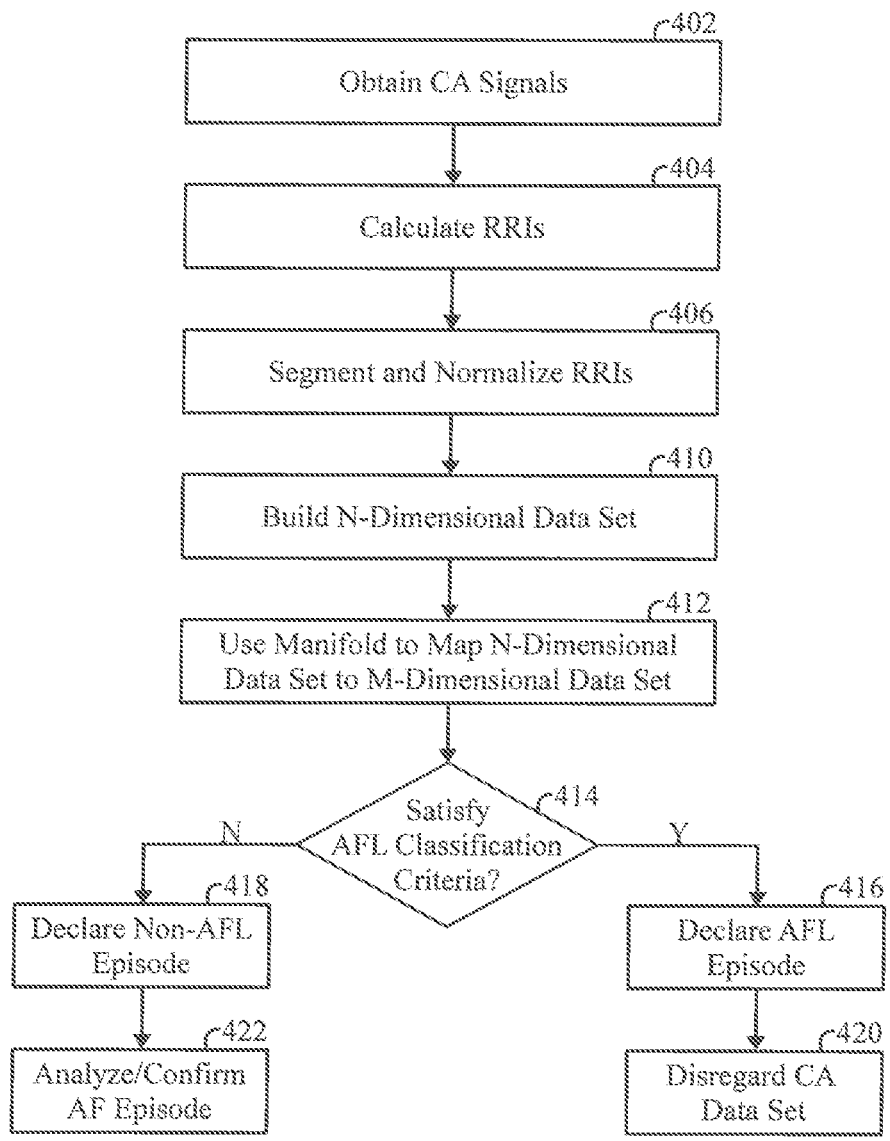
FIG. 4 illustrates a process for utilizing a manifold structure to detect an AFL episode from an N-dimensional data set of CA data values in accordance with embodiments herein.

FIG. 4 illustrates a process for utilizing a manifold structure to detect an AFL episode from an N-dimensional data set of CA data values. The operations of FIG. 4 may be performed in real time by an implantable device. Additionally or alternatively, all or a portion of the operations of FIG. 4 may be performed off-line at a later point in time after CA signals are collected.

At 402, the one or more processors obtain CA signals for a series of beats. At 404, the one or more processors analyze the CA signals to detect R-waves therein and to calculate RR intervals between successive cardiac beats. At 406, the one or more processors divide the RR intervals into RRI segments. Each RRI segment substantially corresponds to one cardiac cycle. At 406, the one or more processors also apply a normalization function to the CA signals to normalize a number of samples in each of the cardiac cycles.

At 410, the one or more processors extract the CA data values at the select sample positions from the CA signals for a desired number of beats. The processors build an N-dimensional data set from the extracted CA data values. Individual dimensions of the N-dimensional data set correspond to an associated sample position along the standard cycle length.

At 412, the one or more processors utilize a manifold structure to map the N-dimensional data set, through nonlinear dimensional reduction, onto an M-dimensional data set.

At 414, the one or more processors compare the M-dimensional data set to one or more AFL classification criteria. The AFL classification criteria may vary depending upon the nature of the dimensions within the M-dimensional data set. For example, an M-dimension may correspond to an average number of peaks in the CA signal, and therefore the corresponding AFL classification criteria may correspond to an AFL peak threshold. As another example, an M-dimension may correspond to an ST length, a power or energy level in the CA signal and the like. The AFL classification criteria may provide that, when X out of the M-dimensions exceed a threshold, an AFL episode is declared. Additionally or alternatively, a boundary may be defined within the M-dimensional space and, when a majority of the beats within the CA data set cross the boundary, an AFL episode may be declared. Additional and alternative AFL classification criteria may be applied.

When the AFL classification criteria are satisfied by the M-dimensional data set, flow moves to 416. When the AFL classification criteria are not satisfied by the M-dimensional data set, flow moves to 418.

At 416, the one or more processors declare the CA data set to include an AFL episode based on the relation between the M-dimensional data set and one or more AFL classification criteria. At 418, the one or more processors declare the CA data set to not include AFL episode (e.g., to represent a non-AFL episode).

Alternative courses of action may occur following the operations at 416, 418, based on the overall nature of the system. For example, when an ICM implements the process of FIG. 4, following 418, at 422, the one or more processors of the ICM may continue to analyze the CA data set for an arrhythmia, such as and atrial fibrillation episode. At 422, the processors of the ICM may also wirelessly transmit the CA data set to a local external device and/or remote server to document the AFL episode and present the information to a clinician. Alternatively, when operation of the ICM moves to 416, at 420, the processors of the ICM may disregard the CA data set and terminate further analysis of the CA data set which is considered to include an AFL episode and thus be unreliable for analysis in connection with arrhythmia detection.

Additionally or alternatively, when a pacemaker, drug delivery or other treatment device (e.g., various IMDs) implement the operations of FIG. 4, following 418, at 422, one or more processors of the IMD may analyze the CA data set for an arrhythmia. At 422, the processors of the IMD may also wirelessly transmit the CA data set to a local external device and/or remote server. When an arrhythmia is detected, the IMD may deliver a therapy. Alternatively, when operation of the IMD moves to 416, at 420, the processors of the IMD may disregard the CA data set and terminate further analysis of the CA data set to avoid delivery of a therapy in the presence of a false positive arrhythmia.

The operations of FIGS. 3A and 4 may be staged to be performed upon the CA signals at various times, such as in real time (e.g., during or shortly after a patient experiences an episode) or at any time after storage of the CA signals. The operations of FIGS. 3A and 4 may be performed by devices and systems at various proximity to a patient with the ICM. For example, the CA signals may be read out of an ICM and transmitted to a local portable external device (e.g., smartphone, table computer, laptop computer, smartwatch, etc.), where the local portable external device locally implements all or a portion of the operations described in connection with FIGS. 3A and 4 while in close proximity to the patient.

The process of FIGS. 3A and 4 may be implemented as part of a first pass process, in which AFL episodes are identified during or before declaration of another arrhythmia episode (e.g., AF). Additionally or alternatively, the process of FIGS. 3A and 4 may be implemented as part of a second pass confirmatory process, in which AFL episodes are identified within a CA data set that has already been analyzed and declared to include one or more arrhythmia episodes (e.g., AFL, AF).

Figure 5A:
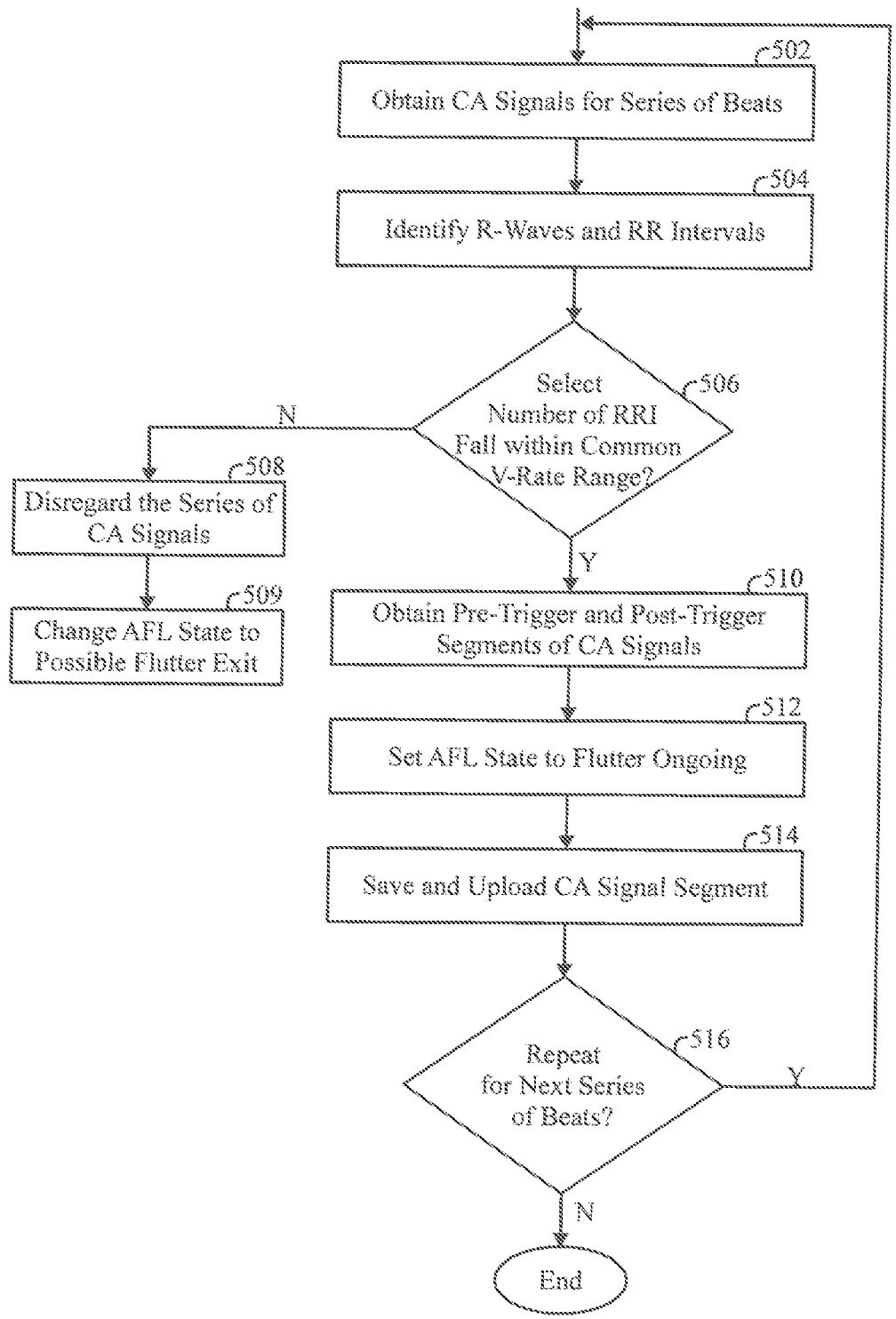
FIG. 5A illustrates a process for detecting entry and/or exit of an AFL episode in accordance with embodiments herein.

FIG. 5A illustrates a process for detecting entry and/or exit of an AFL episode in accordance with embodiments herein. The operations of FIG. 5A may be performed by one or more processors of an ICM, a local external device a remote server, and/or a combination thereof. The operations of FIG. 5A may be performed contemporaneous with, or at a point in time prior to, the operations of FIGS. 4 and/or 3A.

For example, the operations of FIG. 5A may be performed by the ICM in real-time in connection with the operations of FIG. 4. Additionally or alternatively, the operations of FIG. 5A may be performed at a time of implant, periodically and/or during a patient-clinic visit.

At 502, the one or more processors obtain CA signals for a series of cardiac beats (e.g., 10, 16, 25 beats). By way of example, the CA signals may be stored in a circular buffer having sufficient length to store several seconds or minutes of EGM signals. At 502, the processors obtain, from the circular buffer, CA signals for a series of beats that represent a subset of the beats in the circular buffer.

At 504, the one or more processors identify R-waves within the CA signals and add device documented R-wave markers in connection therewith. In addition, at 504, the one or more processors determine RR intervals between successive R-waves within the CA signals. By way of example, the processors may utilize an R-wave detection algorithm as described in patent application Ser. No. 16/007,878, titled "METHOD AND SYSTEM TO DETECT R-WAVES IN CARDIAC ACTIVITY SIGNALS", filed Jun. 13, 2018, the complete subject matter of which is expressly incorporated herein by reference in its entirety.

At 506, the one or more processors determine whether a select number of the RR intervals fall within a predetermined common ventricular rate range. For example, the determination at 506 may detect whether a sequence of R-waves exhibit substantially regular RR intervals. For example, the select number of RR intervals may be programmable (e.g., 16 beats). The determination at 506 may provide an "X of Y" implementation where, for example, 13 out of the last 16 beats would need to be within a common ventricular rate range to satisfy the determination at 506.

FIG. 5B illustrates a table of example ventricular rate ranges that may be utilized for the determination at 506. In FIG. 5B, example AV conduction patterns are illustrated (e.g., 2:1, 3:1, 4:1). Each AV conduction pattern may experience different flutter cycle lengths (in milliseconds). As nonlimiting examples, the AV conduction pattern 2:1 (e.g., 2 atrial beats per 1 ventricular beat) may correspond to flutter cycle lengths of 210 ms, 200 ms and 190 ms. The example flutter cycle lengths also correspond to example ventricular rates, such as 142 bpm, 150 bpm and 158 bpm. The AV conduction pattern 3:1 may correspond to flutter cycle lengths of 210 ms, 200 ms and 190 ms. The example flutter cycle lengths also correspond to example ventricular rates, such as 95 bpm, 100 bpm and 105 bpm. The AV conduction pattern 4:1 may correspond to flutter cycle lengths of 210 ms, 200 ms and 190 ms and ventricular rates of 71 bpm, 75 bpm and 79 bpm. It is recognized that the foregoing numbers are non-limiting examples.

At 506 in FIG. 5A, each RR interval is compared to the ventricular rate ranges (e.g., 142-150 bpm, 95-105 bpm, or 71-79 bpm) in search of highly regular RR intervals at heart rate ranges known to be integer conduction multiples of predetermined AFL rates. The processors determine the number of RR intervals that fall within the common ventricular rate range. Additionally, the processors may apply a clustering criteria to the beats that fall within the common ventricular rate range. For example, the processors may determine whether all of the RR intervals that are within a common ventricular rate range, are also within a predetermined cluster range (e.g., within a number of beats per minute of one another). For example, the processors may determine whether all of the beats within the first range 142-150 bpm, are within 4 bpm cluster criteria of one another.

To further illustrate the foregoing determinations, consider a first string of 16 beats having heart rates [71, 73, 71, 78, 74, 79, 74, 72, 71, 73, 77, 76, 74, 79, 77, 73]. The foregoing first string would not satisfy the trigger at 506 because the beats are spread across the full range of 71-79 bpm and do not satisfy the cluster criteria to be within 4 bpm of one another. Alternatively, consider a second string of heart rates [74, 72, 72, 73, 75, 74, 72, 72, 76, 74, 73, 73, 75, 74, 72, 73]. The foregoing second string would satisfy the determination at 506 and trigger subsequent action because 15 out of the 16 beats are within a cluster criteria of a 4 bpm range of 72-75. Consequently, the second string would serve as a trigger as the processors would identify highly regular RR intervals at heart rate ranges known to be integer conduction multiples of typical AFL rates. It is recognized that the foregoing numbers are merely examples and that alternative numbers of beats may be utilized, as well as an alternative to an "X of Y" implementation.

When the select number of RR intervals do not fall within a common ventricular rate range, flow moves to 508. At 508, the one or more processors discard the series of CA signals as a false AFL episode. At 509, the one or more processors change the AFL state to a possible flutter exit or terminate state.

Alternatively, when the select number of RR intervals do fall within a common ventricular rate range (and optionally also satisfy the clustering criteria), flow moves to 510. At 510, the one or more processors obtain from the circular buffer, discussed above in connection with 502, pre-trigger and post-trigger segments of CA signals that are longer than the series of beats analyzed at 506 and initiating the trigger. For example, the processors may read, from the circular buffer, a 30 second pre-trigger segment of EGM signals preceding the series beats analyzed at 506. In addition, the processors may read, from the circular buffer a 30 second post-trigger segment of CA signals following the series of beats analyzed at 506.

At 512, the one or more processors set a flag designating an AFL state to flutter ongoing state to indicate that the processors have determined that an possible AFL episode is ongoing. The flutter ongoing state will remain on until the select criteria are satisfied at 506 to indicate that a possible flutter exit has occurred.

At 514, the one or more processors store the CA signals, RR intervals and/or the CA data set (e.g., CA signals, markers and other information) for the series of beats analyzed at 506, as well as the pre-trigger and post-trigger segments of CA signals obtained at 510. For example, the processors store the second string of heart rates described above, along with preceding and following 30 second strips of EGM signals, for later analysis by the ICM or IMD. Optionally, the CA signals, RR intervals and/or the CA data set for the second string of heart rates (and pre-trigger and post-trigger CA signals) may be uploaded from an ICM or IMD to a local external device and/or to a remote server. The local eternal device and/or remote server would then implement the analysis. The CA signals and/or the CA data set may be analyzed in real time and/or off-line to classify the candidate AFL episode as a true AFL episode or as a non-AFL episode that is discarded.

By applying the determination for regular RR intervals with integer conduction multiples of typical AFL rates, the operations of FIG. 5A avoid visibly presenting the candidate AFL episode to a clinician, avoid triggering an alert that may be pushed to a clinic and other AFL declaration related actions. Instead, the determination at 506 merely triggers storage and uploading of the CA signals for further analysis and discrimination.

Optionally, the operation at 508 may be omitted and the CA signals for the analyzed series of beats may not be discarded, but instead recorded as a possible flutter exit and uploaded to a local external device and/or remote server. When the CA signals for a possible flutter exit are saved and uploaded, preceding and following segments of CA signals may be saved and uploaded there with.

At 516, the one or more processors determine whether to repeat the operations of FIG. 5A in connection with a next series of beats. When the operations of FIG. 5A are to be repeated, an index is stepped forward a predetermined number of beats within the circular buffer saving the CA signals. For example, the index may step forward one beat or a greater number of beats. When the index is stepped forward one beat, the operations of FIG. 5A are repeated for a next series of beats that substantially overlaps a previously analyzed series of beats, but for the indexed beat(s). The operations of FIG. 5A may be continuously performed as the content of the circular buffer is similarly continuously updated.

The present description is in connection with an ICM type of implantable medical device. Optionally, embodiments may be implemented in connection with one or more other types of implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method and System to Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable and Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method and System for Identifying a Potential Lead Failure in an Implantable Medical Device" and U.S. Pat. No. 9,232,485 "System And Method For Selectively Communicating With An Implantable Medical Device", which are hereby incorporated by reference.

In the foregoing examples, the processors and memory are described to be housed within an implantable device, such as an ICM and/or IMD. Additionally or alternatively, the processors and memory may be housed within at least one of a local external device and a remote server.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc.

Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Pen, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A computer implemented method for declaring arrhythmias in cardiac activity, comprising:
   under control of one or more processors configured with specific executable instructions,
   obtaining far field cardiac activity (CA) signals for a series of beats;
   building an N-dimensional data set from data values for features of interest from the CA signals;
   utilizing a manifold structure to map the N-dimensional data set, through nonlinear dimensional reduction, onto an M-dimensional data set, wherein N is greater than M; and
   declaring an atrial fibrillation (AFL) episode based on a relation between the M-dimensional data set and one or more AFL classification criteria.

2. The method of claim 1, where the manifold structure utilizes locally linear embedding to provide the nonlinear dimensional reduction to form the M-dimensional data set.

3. The method of claim 1, wherein N is greater than or equal to 100 dimensions, and wherein M is less than or equal to 10 dimensions.

4. The method of claim 1, further comprising dividing the CA signals into RR interval (RRI) segments that are normalized to a select cycle length having a common number of non-prioritized sample positions during each of the RRI segments, and wherein the building operation comprises populating dimensions of the N-dimensional data set with CA data values for the non-prioritized sample positions from the RRI segments.

5. The method of claim 4, wherein the dimensions of the N-dimensional data set correspond to the non-prioritized sample positions along the select cycle length.

6. The method of claim 1, further comprising automatically calculating the manifold structure utilizing the nonlinear dimensionality reduction to automatically determines an underlying structure of data points within the N-dimensional data set.

7. The method of claim 1, further comprising programming the manifold structure into firmware of an implantable device to configure the implantable device to utilize the manifold structure in real time in connection with declaring AFL episodes.

8. The method of claim 1, further comprising analyzing the N-dimensional data set, at a local external or remote server, to automatically calculate the manifold structure based on locally linear embedding to provide the nonlinear dimensional reduction.

9. The method of claim 1, further comprising determining whether a select number of RRI segments from the CA signals fall within a predetermined common ventricular rate range, wherein the predetermined common ventricular rate range corresponds to an integer conduction multiple of a predetermined AFL rate, and based on the determining, declaring a candidate AFL episode to be analyzed through the building, utilizing and declaring operations.

10. The method of claim 9, wherein the declaring the candidate AFL episode further comprises applying a clustering criteria to the RRI segments of the CA signals that fall within the predetermined common ventricular rate range, the clustering criteria corresponds to a predetermined number of RRI segments falling within a predetermined cluster range of one another.

11. A system for declaring arrhythmias in cardiac activity, comprising:
  memory to store specific executable instructions;
  one or more processors configured to execute the specific executable instructions for:
    obtaining far field cardiac activity (CA) signals for a series of beats;
    building an N-dimensional data set from data values for features of interest from the CA signals;
    utilizing a manifold structure to map the N-dimensional data set, through nonlinear dimensional reduction, onto an M-dimensional data set, wherein N is greater than M; and
    declaring an atrial fibrillation (AFL) episode based on a relation between the M-dimensional data set and one or more AFL classification criteria.

12. The system of claim 11, where the manifold structure utilizes locally linear embedding to provide the nonlinear dimensional reduction to form the M-dimensional data set.

13. The system of claim 11, wherein N is greater than or equal to 100 dimensions, and wherein M is less than or equal to 10 dimensions.

14. The system of claim 11, wherein the one or more processors are further configured to divide the CA signals into RR interval (RRI) segments that are normalized to a select cycle length having a common number or non-prioritized sample positions during each of the RRI segments, and to populate dimensions of the N-dimensional data set with CA data values for the non-prioritized sample positions from the RRI segments.

15. The system of claim 11, wherein the one or more processors are further configured to automatically calculate the manifold structure utilize a utilizing the non-linear dimensionality reduction to automatically determines an underlying structure of data points within the N-dimensional data set.

16. The system of claim 11, further comprising an implantable device that houses the memory and the one or more processors, the memory configured to store the manifold structure, the one or more processors configured to utilize the manifold structure in real time in connection with declaring AFL episodes.

17. The system of claim 11, further comprising external device or server that houses the one or more processors that are further configured to analyze the N-dimensional data set to automatically calculate the manifold structure based on locally linear embedding to provide the nonlinear dimensional reduction.

18. The system of claim 11, the one or more processors further configured to determine whether a select number of RR interval (RRI) segments from the CA signals fall within a predetermined common ventricular rate range, wherein the predetermined common ventricular rate range corresponds to an integer conduction multiple of a predetermined AFL rate, and based on the determining, to declare a candidate AFL episode to be analyzed through the building, utilizing and declaring operations.

19. The system of claim 11, further comprising an implantable medical device housing the one or more processors and memory.

20. The system of claim 11, wherein the one or more processors and memory are housed within at least one of an external device or a server.

* * * * *